(12) United States Patent
Liu et al.

(10) Patent No.: US 12,416,563 B2
(45) Date of Patent: Sep. 16, 2025

(54) SYSTEMS AND METHODS TO DETERMINE PERMEABILITY OF ROCK UNDER ANISOTROPIC STRESS

(71) Applicant: ARAMCO SERVICES COMPANY, Houston, TX (US)

(72) Inventors: Hui-Hai Liu, Katy, TX (US); Jilin Zhang, Houston, TX (US); Mohammed Boudjatit, El Kennar (DZ); Gary Eppler, Baytown, TX (US)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 312 days.

(21) Appl. No.: 18/324,857

(22) Filed: May 26, 2023

(65) Prior Publication Data
US 2024/0393223 A1   Nov. 28, 2024

(51) Int. Cl.
*G01N 15/08* (2006.01)
*G01N 33/24* (2006.01)

(52) U.S. Cl.
CPC ........... *G01N 15/082* (2013.01); *G01N 33/24* (2013.01)

(58) Field of Classification Search
CPC ....... G01N 15/08; G01N 15/082; G01N 33/24
See application file for complete search history.

(56) References Cited

U.S. PATENT DOCUMENTS 5,226,310 A * 7/1993 Steiger ..................... G01N 3/10
                                                    73/794

FOREIGN PATENT DOCUMENTS

CN    114841019 A     8/2022
FR    2734364 A1 *   11/1996   ........... E21B 49/006

OTHER PUBLICATIONS

Heller, Rob, et al. "Experimental Investigation of Matrix Permeability of Gas Shales." AAPG Bulletin, vol. 98, No. 5, May 2014, pp. 975-995 (21 pages).*
Machine Translation of FR 2734364 A1 (Year: 2016).*
Cao, Wenzhuo, Qinghua Lei, and Wu Cai. "Stress-dependent deformation and permeability of a fractured coal subject to excavation-related loading paths." Rock Mechanics and Rock Engineering 54.8 (2021): 4299-4320 (22 pages).

(Continued)

*Primary Examiner* — Nathaniel J Kolb
(74) *Attorney, Agent, or Firm* — Osha Bergman Watanabe & Burton LLP

(57) ABSTRACT

Methods and systems are disclosed. The methods may include determining a first sequence of permeabilities by subjecting a rock sample to a first sequence of confining stress, axial stress, pore pressure (CSASPP) triplets and determining a first rock parameter using the first sequence of permeabilities, the first sequence of CSASPP triplets, and a first permeability model. The methods may further include determining a second sequence of permeabilities by subjecting the rock sample to a second sequence of CSASPP triplets and determining a second rock parameter using the second sequence of permeabilities, the second sequence of CSASPP triplets, and the first permeability model. The method may still further include determining an in situ permeability for an in situ rock based on an initial permeability, a second stress sensitivity parameter, a first stress sensitivity parameter, a confining stress value, axial stress values, a pore pressure value, and a second permeability model.

20 Claims, 11 Drawing Sheets

(56) References Cited

OTHER PUBLICATIONS

Jones, S. C. "A Technique for Faster Pulse-Decay Permeability Measurements in Tight Rocks." SPE Formation Evaluation, vol. 12, No. 01, Mar. 1997, pp. 19-25 (7 pages).
Luffel, D.L., et al. "Matrix Permeability Measurement of Gas Productive Shales." Society of Petroleum Engineers 26633, Oct. 1993, pp. 261-270 (10 pages).
Meredith, P. et al.; "An experimental study of elastic wave propagation anisotropy and permeability anisotropy in an Ilitic shale." SPE/ISRM 47369 Rock Mechanics in Petroleum Engineering, Jul. 1998 (7 pages).

\* cited by examiner

SYSTEMS AND METHODS TO DETERMINE PERMEABILITY OF ROCK UNDER ANISOTROPIC STRESS

BACKGROUND

Rock within a subterranean region of interest may be composed of grains and pores. Fluids, such as carbon dioxide, water, brine, and hydrocarbons, may permeate those pores. Further, the fluids may flow through the pores of the rock. A measure of how easily the fluids flow is known as permeability. As geological processes, such as the deposition of overburden rock, occur within the subterranean region of interest, increased effective stress applied to the rock may reduce permeability. Reduced permeability may limit fluid flow to make fluid extraction more difficult. As such, quantifying the permeability of rock under various anisotropic stress conditions may be useful in predicting fluid production rates, specifically hydrocarbon production rates.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a method. The method includes obtaining, from a subterranean region of interest, a rock sample having a rock type, determining a first sequence of permeabilities by subjecting the rock sample, using a permeability system, to a first sequence of confining stress, axial stress, pore pressure (CSASPP) triplets, where the first sequence of CSASPP triplets includes a constant confining stress, and determining a first rock parameter using the first sequence of permeabilities, the first sequence of CSASPP triplets, and a first permeability model, where the first permeability model includes a first stress model, where the first stress model includes a first stress sensitivity parameter. The method further includes determining a second sequence of permeabilities by subjecting the rock sample, using the permeability system, to a second sequence of CSASPP triplets, where the second sequence of CSASPP triplets includes a constant axial stress, determining a second rock parameter using the second sequence of permeabilities, the second sequence of CSASPP triplets, and the first permeability model, and determining the first stress sensitivity parameter based, at least in part, on the first rock parameter and the second rock parameter. The method still further includes determining an initial permeability and a second stress sensitivity parameter based, at least in part, on the first sequence of CSASPP triplets, the first sequence of permeabilities, the second sequence of CSASPP triplets, the second sequence of permeabilities, the first stress sensitivity parameter, and the first permeability model, obtaining a confining stress value, axial stress values, and a pore pressure value for an in situ rock in the subterranean region of interest, where the in situ rock is of the rock type, and determining an in situ permeability for the in situ rock based, at least in part, on the initial permeability, the second stress sensitivity parameter, the first stress sensitivity parameter, the confining stress value, the axial stress values, the pore pressure value, and a second permeability model, where the second permeability model includes a second stress model.

In general, in one aspect, embodiments relate to a system. The system includes a permeability system configured to subject a rock sample, from a subterranean region of interest, having a rock type to a first sequence of CSASPP triplets and a second sequence of CSASPP triplets. The system further includes a computer system configured to determine a first sequence of permeabilities following the rock sample being subjected to the first sequence of CSASPP triplets using the permeability system, where the first sequence of CSASPP triplets includes a constant confining stress, determine a first rock parameter using the first sequence of permeabilities, the first sequence of CSASPP triplets, and a first permeability model, where the first permeability model includes a first stress model, where the first stress model includes a first stress sensitivity parameter, and determine a second sequence of permeabilities following the rock sample being subjected to the second sequence of CSASPP triplets using the permeability system, where the second sequence of CSASPP triplets includes a constant axial stress. The computer system is further configured to determine a second rock parameter using the second sequence of permeabilities, the second sequence of CSASPP triplets, and the first permeability model, determine the first stress sensitivity parameter based on the first rock parameter and the second rock parameter, and determine an initial permeability and a second stress sensitivity parameter based on the first sequence of CSASPP triplets, the first sequence of permeabilities, the second sequence of CSASPP triplets, the second sequence of permeabilities, the first stress sensitivity parameter, and the first permeability model. The computer system is further still configured to receive a confining stress value, axial stress values, and a pore pressure value for an in situ rock in the subterranean region of interest, where the in situ rock is of the rock type and determine an in situ permeability for the in situ rock based, at least in part, on the initial permeability, the second stress sensitivity parameter, the first stress sensitivity parameter, the confining stress value, the axial stress values, the pore pressure value, and a second permeability model, where the second permeability model includes a second stress model.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
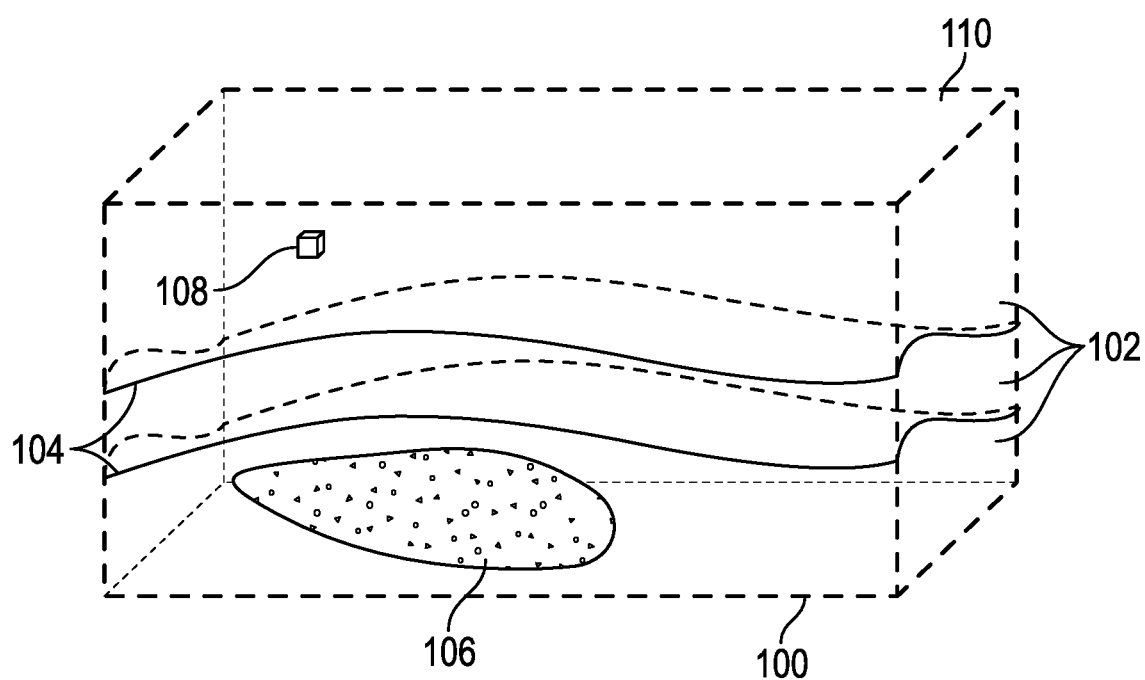
FIG. 1 illustrates a subterranean region of interest in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a pore pressure" includes reference to one or more of such pressures.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowchart may be omitted, repeated, and/or performed in a different order than the order shown. Accordingly, the scope disclosed herein should not be considered limited to the specific arrangement of steps shown in the flowchart.

Although multiple dependent claims are not introduced, it would be apparent to one of ordinary skill that the subject matter of the dependent claims of one or more embodiments may be combined with other dependent claims.

In the following description of FIGS. 1-10, any component described regarding a figure, in various embodiments disclosed herein, may be equivalent to one or more like-named components described regarding any other figure. For brevity, descriptions of these components will not be repeated regarding each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described regarding a corresponding like-named component in any other figure.

Methods and systems are disclosed to determine in situ permeability for in situ rock within a subterranean region of interest. In a laboratory setting, a rock sample from the subterranean region of interest may be tested to determine a first sensitivity parameter assuming a first permeability model. The first permeability model may then be extended to a second permeability model such that the second permeability model and the first stress sensitivity parameter, among other values, may be used to determine the in situ permeability of the in situ rock. The in situ permeability of the in situ rock may then be used to determine a hydrocarbon production rate.

Turning to FIG. 1, FIG. 1 illustrates a subterranean region of interest (100) in accordance with one or more embodiments. The subterranean region of interest (100) may consist of layers of rock (102) separated by geological boundaries (104). Some layers of rock (102) may reside above a hydrocarbon reservoir (106). Layers of rock (102) that reside above a hydrocarbon reservoir (106) may be referred to as "overburden rock." The hydrocarbon reservoir (106) may be rock from which hydrocarbons are generated (hereinafter "source rock") or may be adjacent to source rock (102). For example, an unconventional hydrocarbon reservoir (106) may be shale rock. Hereinafter, any rock within a subterranean region of interest (100) may be denoted "in situ rock" or simply "rock."

In situ rock (102) at different positions (108) within the subterranean region of interest (100) may be in different stress states. Note that stress is a normalized measure of force, in particular a force per cross-sectional area. The stress state of in situ rock (102) at each position (108) may be caused, in part, by the types and degree of geological conditions and/or manmade activities affecting the in situ rock (102). Geological conditions may include, but are not limited to, the weight of overburden rock, tectonics, thermal processes, and glacial rebound. For example, in situ rock (102) deep within the subterranean region of interest (100) may present a higher stress state relative to in situ rock (102) of the same rock type near the surface (110) due to the weight of overburden rock. Manmade activities may include, but are not limited to, drilling a well, well completion strategies, hydrocarbon or other fluid recovery, and mining tunnels. For example, drilling a well within the subterranean region of interest (100) may result in cracked or weakened in situ rock (102) that presents a lower stress state relative to the stress state of the in situ rock (102) at that position (108) prior to drilling the well.

Figure 2A:
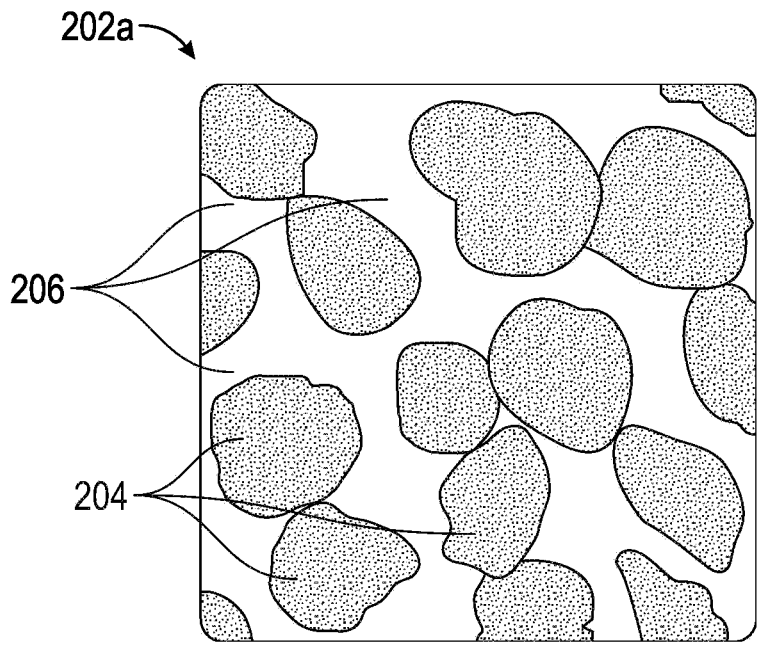
FIGS. 2A and 2B illustrate rock in accordance with one or more embodiments.
Figure 2B:
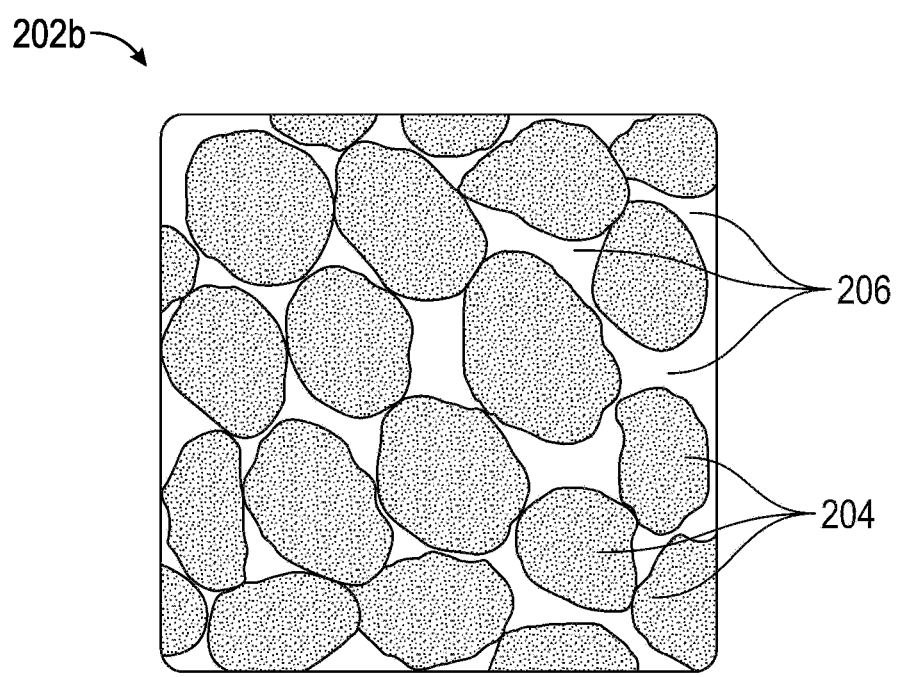

The stress state of in situ rock (102) may affect each constituent of in situ rock (102), in particular, the grains and pores of in situ rock (102). Turning to FIGS. 2A and 2B, the constituents of in situ rock (202*a, b*) may include grains (204) and pores (206). The grains (204) may be a material made up of, but not limited to, quartz, calcite, or kerogen. The material of the grains (204) may be a key consideration in determining the "rock type" of the in situ rock (202*a, b*). The pores (206) are voids between the grains (204). The pores (206) may be saturated with fluid. The fluid may be, but is not limited to, air, water, brine, natural gas, oil, other hydrocarbons, or any mixture thereof. For example, the rock (202*a, b*) of an unconventional hydrocarbon reservoir (106) may consist of kerogen grains (204) (i.e. source rock) with hydrocarbon-saturated pores (206).

The material of the grains (204) and the fluid saturating the pores (206) of the rock (202a, b) may dictate the physical properties, mechanical properties, and mechanical parameters of the rock (202a, b). Physical properties include, but are not limited to, porosity and permeability. Porosity is defined as the fraction of the volume of the rock (202a, b) that is occupied by the pores (206). For example, unconventional hydrocarbon reservoirs (106) may have a low porosity under 5%. Permeability is closely related to porosity. Permeability is a measure of how easily fluid flows through the rock (202a, b). The degree of connection between the pores (206) and the viscosity of the fluid saturating the pores (206) may constrain permeability. Thus, FIG. 2A may depict rock (202a) with high porosity and high permeability, while FIG. 2B may depict rock (202b) with low porosity and low permeability. Note that high porosity, low permeability rock and low porosity, high permeability rock can also exist.

Figure 3:
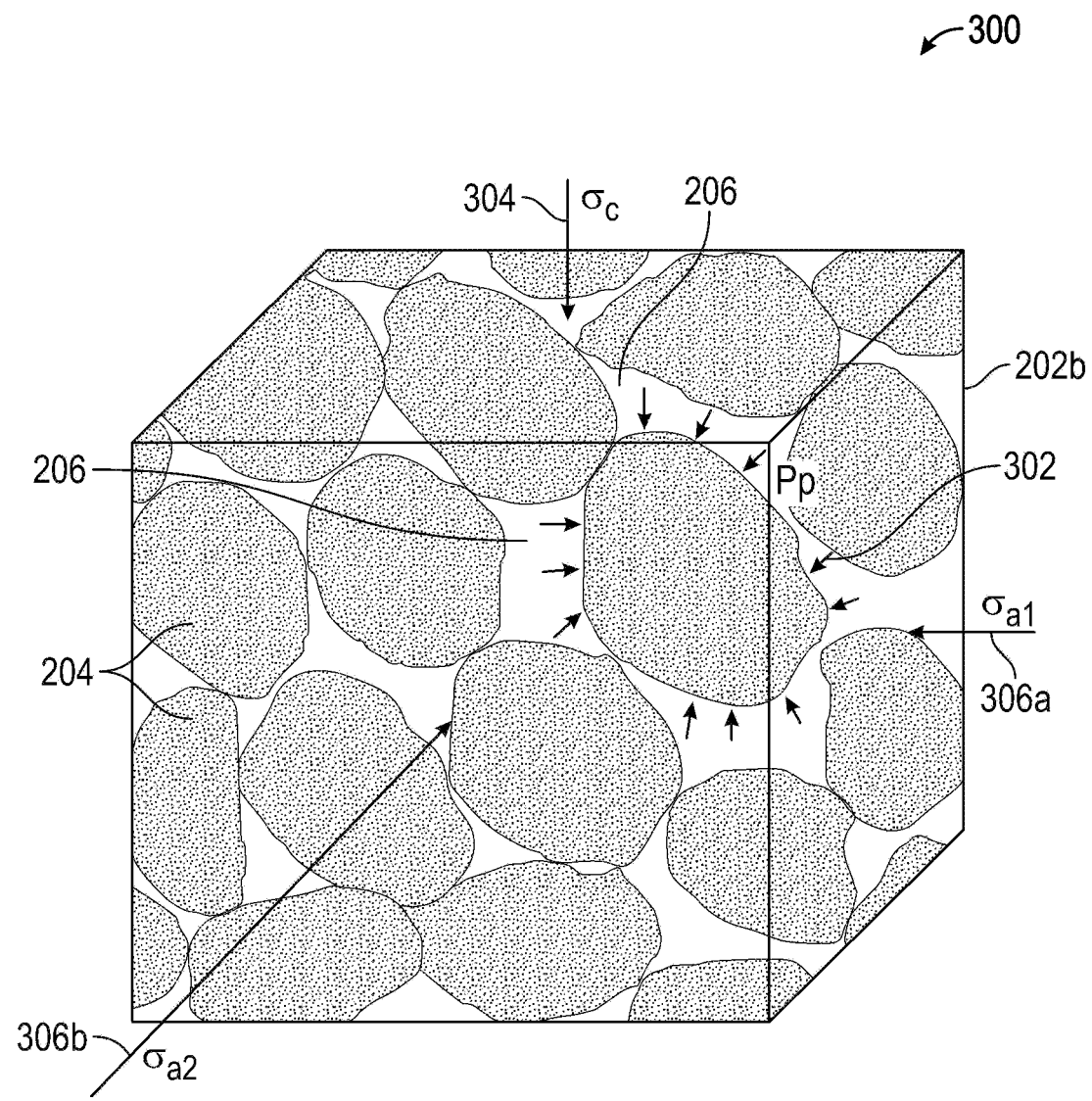
FIG. 3 illustrates a stress state of rock in accordance with one or more embodiments.

Turning to FIG. 3, FIG. 3 illustrates a stress state (300) of a rock (202b) in accordance with one or more embodiments. The stress state (300) of the rock (202b) may include, but are not limited to, the mechanical properties of pore pressure $p_p$ (302), confining stress $\sigma_c$ (304) (alternatively "overburden stress"), one or more axial stresses $\sigma_{a1}$ and $\sigma_{a2}$ (306a, b), deviatoric stress $\sigma_d$, and effective stress $\sigma_e$.

Pore pressure $p_p$ (302) is the pressure associated with the fluids saturating the pores (206) of the rock (202b). In some embodiments, the pore pressure $p_p$ (302) may be considered hydrostatic or at equilibrium. Confining stress $\sigma_c$ (304) is the stress caused by overburden rock. As such, confining stress $\sigma_c$ (304) may be alternatively referred to as overburden stress or "vertical stress." Each axial stress $\sigma_{a1}$ and $\sigma_{a2}$ (306a, b) may be the stress caused by a lateral or horizontal stress. When $\sigma_{a1} = \sigma_{a2}$, the axial stress will be generically referred to using the symbol $\sigma_a$. Deviatoric stress $\sigma_d$ may be a difference of stresses. In some embodiments, deviatoric stress $\sigma_d$ may be defined as:

$$\sigma_d = \sigma_a - \sigma_c. \qquad \text{Equation (1)}$$

Continuing, effective stress $\sigma_e$ may be a function of pore pressure $p_p$ (302), confining stress $\sigma_c$ (304), one or more axial stresses $\sigma_{a1}$ and $\sigma_{a2}$ (306a, b), and/or deviatoric stress $\sigma_d$. In some embodiments, the effective stress $\sigma_e$ may be modeled as:

$$\sigma_e = \sigma_c - \beta p_p, \qquad \text{Equation (2)}$$

where $\beta$ is a Biot coefficient. The Biot coefficient $\beta$ may be a measure of the bulk modulus of the rock (202b) void of fluid relative to the bulk modulus of only the grains (204) of the rock (202b). Further, the Biot coefficient $\beta$ may range between zero and one. Further still, the Biot coefficient $\beta$ may be considered a mechanical parameter. The effective stress $\sigma_e$ as modeled by Equation (2) may be thought of as the stress that controls the mechanical behavior of the rock (202b) where the confining stress $\sigma_c$ (304) is supported by the grains (204) and a portion of the pore pressure $p_p$ (302) supports the grains (204). Defining effective stress $\sigma_e$ using Equation (2) may model an "isotropic" stress state (300) of rock (202b) as confining stress $\sigma_c$ (304) is considered equal in all three orthogonal directions.

In other embodiments, the effective stress $\sigma_e$ may be modeled as:

$$\sigma_e = \sigma_c + \gamma \sigma_d - \beta p_p, \qquad \text{Equation (3)}$$

where $\sigma_d$ is given in Equation (1) and $\gamma$ is a first stress sensitivity parameter. In embodiments that define effective stress $\sigma_e$ using Equation (3), the first stress sensitivity parameter $\gamma$ may alternatively be referred to as a "deviatoric stress sensitivity parameter" as the parameter scales the deviatoric stress $\sigma_d$. The first stress sensitivity parameter $\gamma$ may be another mechanical parameter. Defining effective stress $\sigma_e$ using Equation (3) may model an "anisotropic" stress state (300) of rock (202b) as confining stress $\sigma_c$ (304) and one axial stress $\sigma_a$ are considered unequal. Hereinafter, Equation (3) will be considered a "first stress model" that corresponds to the condition where the two axial stresses $\sigma_{a1}$ and $\sigma_{a2}$ (306a, b) are equal. A person of ordinary skill in the art will appreciate that other first stress models may be used without departing from the scope of the disclosure.

In still other embodiments, the effective stress $\sigma_e$ may be modeled as:

$$\sigma_e = (1 - 2\gamma)\sigma_c + \gamma(\sigma_{a1} + \sigma_{a2}) - \beta p_p. \qquad \text{Equation (4)}$$

Defining effective stress $\sigma_e$ using Equation (4) may also model an "anisotropic" stress state (300) of rock (202b) as confining stress $\sigma_c$ (304) and both axial stresses $\sigma_{a1}$ and $\sigma_{a2}$ (306a, b) are considered. Hereinafter, Equation (4) will be considered a "second stress model" that corresponds to the condition where the two axial stresses $\sigma_{a1}$ and $\sigma_{a2}$ (306a, b) are different. However, a person of ordinary skill in the art will appreciate that other second stress models may be used without departing from the scope of the disclosure.

Effective stress $\sigma_e$, as modeled by Equations (2)-(4), may be used, in part, to model permeability k of rock (202b). In some embodiments, permeability k may be modeled as:

$$k = k_0 e^{-\alpha \sigma_e}, \qquad \text{Equation (5)}$$

where $k_0$ is an initial permeability when the effective stress $\sigma_e$ is zero and $\alpha$ is a second stress sensitivity parameter. The second stress sensitivity parameter $\alpha$ may be yet another mechanical parameter. Based on Equation (5), permeability k may exponentially decrease as effective stress $\sigma_e$ increases. As such, the stress state (300) of in situ rock (202b) may affect the in situ permeability k of the rock (202b). A person of ordinary skill in the art will appreciate that permeability k may be modeled different than Equation (5) without departing from the scope of the disclosure. Hereinafter, Equation (5) is considered a "permeability model." In some embodiments, a "first permeability model" may include Equation (3) embedded into Equation (5). In some embodiments, a "second permeability model" may include Equation (4) embedded into Equation (5).

An anisotropic stress state (300) of in situ rock (202b) may be mimicked in a laboratory setting. Note that for practical convenience, the two axial stresses $\sigma_{a1}$ and $\sigma_{a2}$ (306a, b) may be equal during testing in the laboratory setting and, thus, denoted as $\sigma_a$. Mimicking an anisotropic stress state (300) of in situ rock (202b) may allow for permeability k to be determined. In turn, the first stress sensitivity parameter γ may be determined using the anisotropic stress state (300) and the permeability k.

Figure 4A:
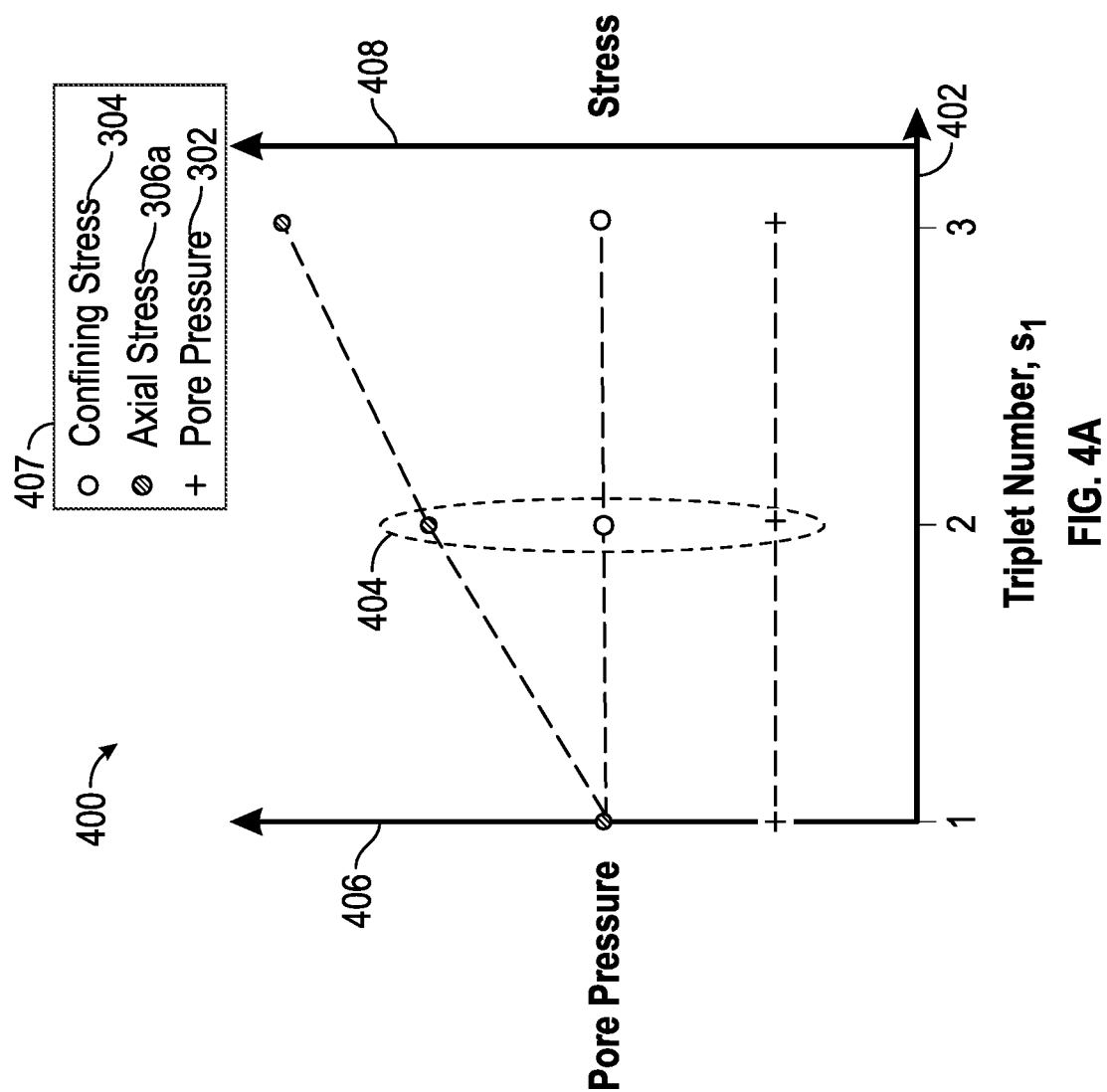
FIG. 4A shows a first sequence of confining stress, axial stress, pore pressure triplets in accordance with one or more embodiments.

An anisotropic stress state (300) of in situ rock (202b) may be mimicked in a laboratory setting by subjecting a rock sample to confining stress, axial stress, pore pressure (CSASPP) triplets. FIG. 4A illustrates a first sequence of CSASPP triplets (400) in accordance with one or more embodiments. The abscissa (402) presents the ordering of the first sequence of CSASPP triplets (400) designated by triplet number $s_1$ one through three. However, any number of CSASPP triplets (404) may make up the first sequence of CSASPP triplets (400) without departing from the scope of the disclosure. The left ordinate (406) presents pore pressure $p_p$ (302) and the right ordinate (408) presents stress, which may be confining stress $\sigma_c$ (304) or axial stress $\sigma_a$, as shown by the key (407). Note that while pressure and stress are different, the units of pressure and stress may be the same. The first sequence of CSASPP triplets (400) is defined such that confining stress $\sigma_c$ (304) is constant. The value of the axial stress $\sigma_a$ (306a) may be independent of the value of the confining stress $\sigma_c$ (304). Further still, in some embodiments, the pore pressure(s) $p_p$ (302) may be greater than approximately 17 megapascals (MPa) (or approximately 2500 pounds per square inch (psi)) to minimize Knudsen diffusion.

As shown by the key (407), each open circle denotes a value of a confining stress $\sigma_c$ (304), each closed circle denotes a value of an axial stress $\sigma_a$ (306a), and each cross denotes a value of a pore pressure $p_p$ (302) among the first sequence of CSASPP triplets (400). The rock sample may be subjected to each CSASPP triplet (404) among the first sequence of CSASPP triplets (400) statically in order as designated by the triplet number $s_1$.

Figure 4B:
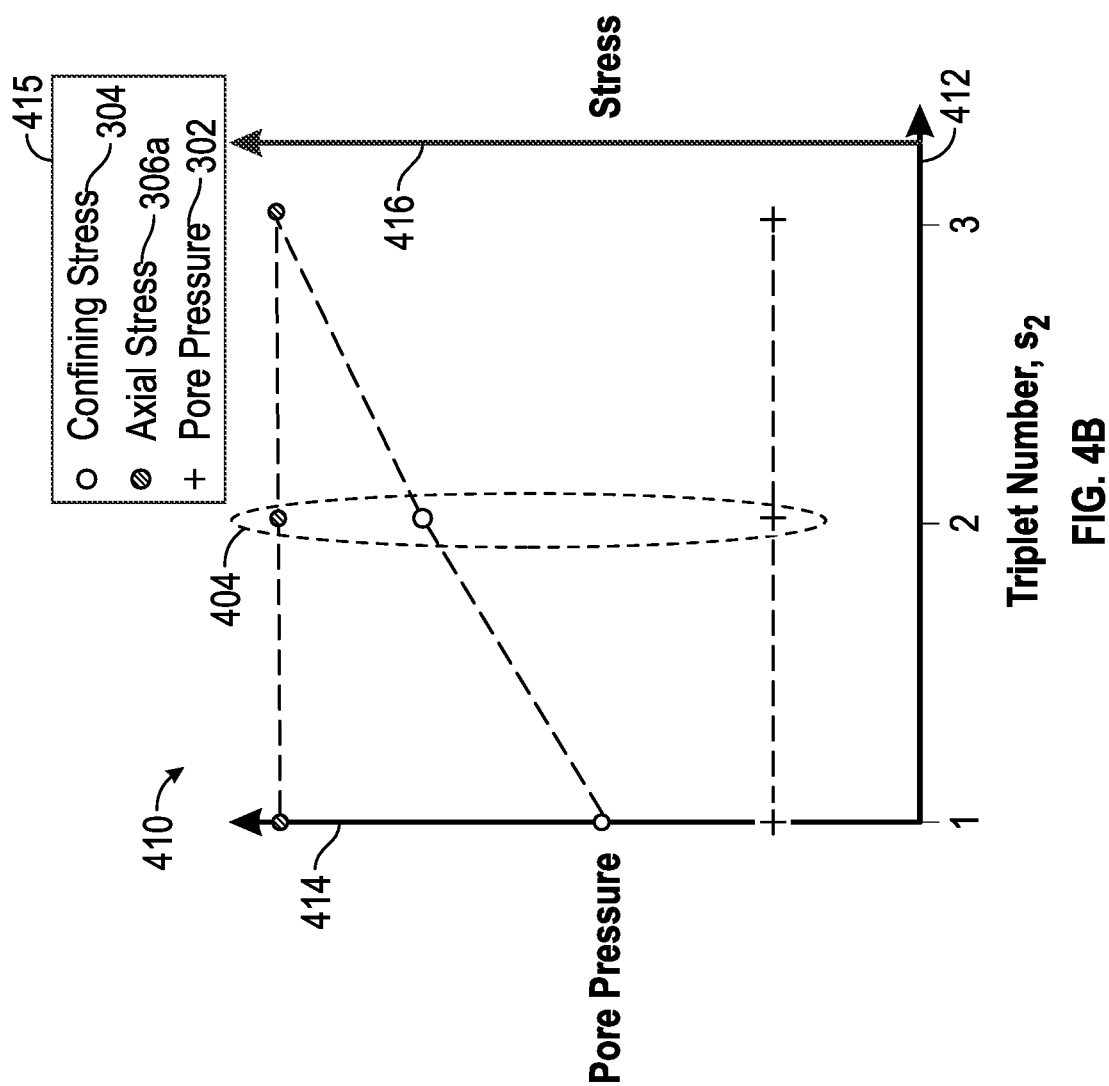
FIG. 4B shows a second sequence of confining stress, axial stress, pore pressure triplets in accordance with one or more embodiments.

FIG. 4B illustrates a second sequence of CSASPP triplets (410) in accordance with one or more embodiments. The abscissa (412) presents the ordering of the second sequence of CSASPP triplets (410) designated by triplet number $s_2$ one through three. However, any number of CSASPP triplets (404) may be included in the second sequence of CSASPP triplets (410) without departing from the scope of the disclosure. The left ordinate (414) presents pore pressure $p_p$ (302) and the right ordinate (416) presents stress, which may be confining stress $\sigma_c$ (304) or axial stress $\sigma_a$ (306a), as shown by the key (415). The second sequence of CSASPP triplets (410) is defined such that axial stress $\sigma_a$ (306a) is constant. The value of the axial stress $\sigma_a$ (306a) may be independent of the value of the confining stress $\sigma_c$ (304). Further, in some embodiments, the pore pressure(s) $p_p$ (302) may be greater than approximately 17 megapascals (MPa) (or approximately 2500 pounds per square inch (psi)) to minimize Knudsen diffusion.

As shown by the key (415), each open circle denotes a value of a confining stress $\sigma_c$ (304), each closed circle denotes a value of an axial stress $\sigma_a$ (306a), and each cross denotes a value of a pore pressure $p_p$ (302) among the second sequence of CSASPP triplets (410). The rock sample may be subjected to each CSASPP triplet (404) among the second sequence of CSASPP triplets (410) statically in order as designated by the triplet number $s_2$.

In some embodiments, a rock sample may be subjected to the first sequence of CSASPP triplets (400) and then the second sequence of CSASPP triplets (410) or vice versa. In other embodiments, one rock sample may be subjected to the first sequence of CSASPP triplets (400) and another rock sample of the same rock type as the first rock sample may be subjected to the second sequence of CSASPP triplets (410).

To apply the first sequence of CSASPP triplets (400) and the second sequence of CSASPP triplets (410) to a rock sample in a laboratory setting, a rock sample must first be obtained from a subterranean region of interest (100). A rock sample may be obtained from a subterranean region of interest (100) using a rock sample extraction tool. In some embodiments, the rock sample extraction tool may be a coring system that is used to simultaneously drill a well and retrieve a rock core.

Figure 5:
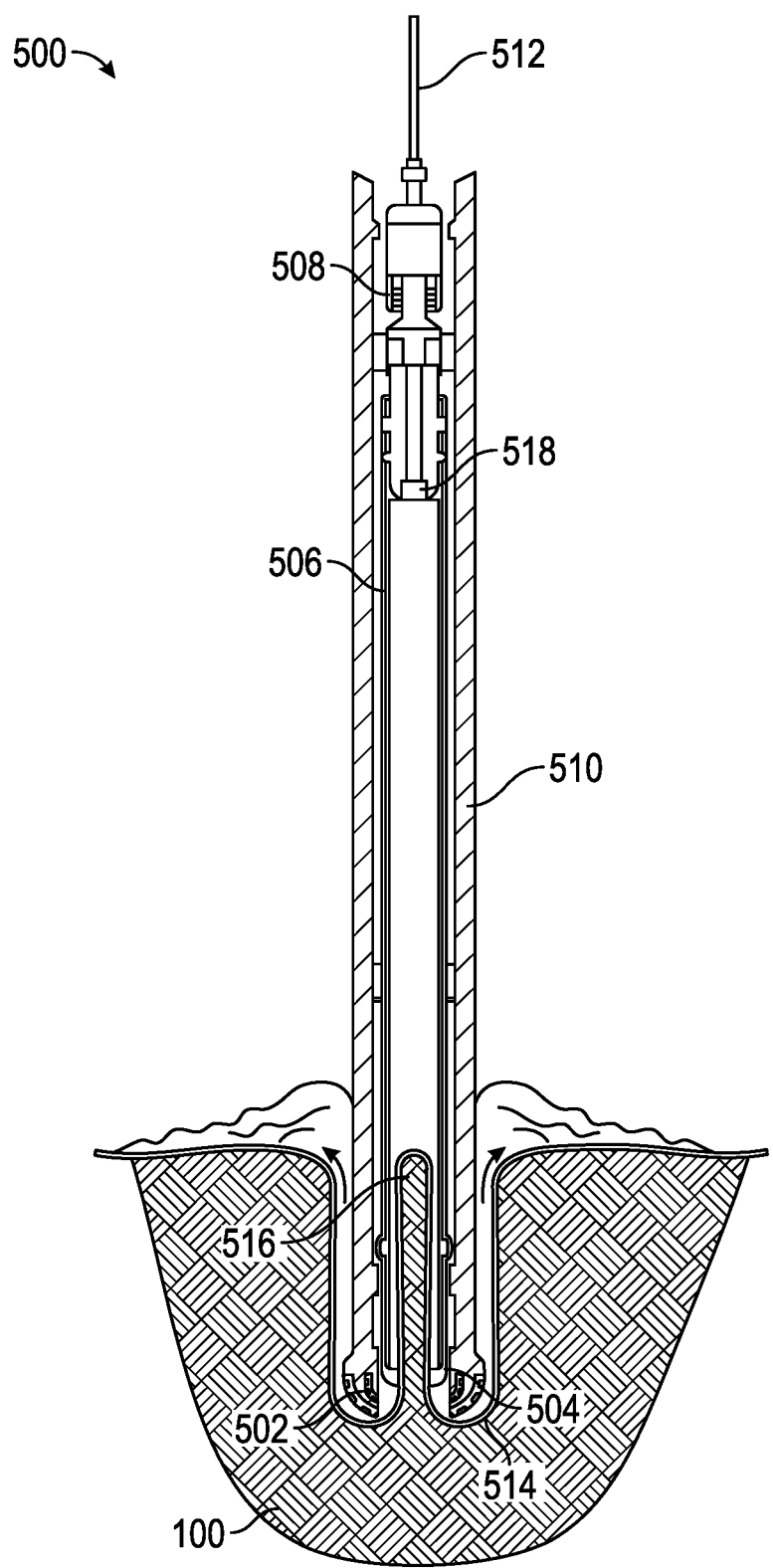
FIG. 5 illustrates a coring system in accordance with one or more embodiments.

FIG. 5 illustrates a coring system (500) in accordance with one or more embodiments. The coring system (500) may consist of a core bit (502), core catcher (504), inner barrel (506), swivel (508), and outer barrel (510) among other components. In some embodiments, the core catcher (504) and inner barrel (506) may be suspended by the swivel (508) while the outer barrel (510) may mate with the core bit (502) and a drillstring (512). The coring system (500) may be deployed within a subterranean region of interest (100) using the drillstring (512). As the core bit (502) rotates to drill a well (514) within the subterranean region of interest (100), the core bit (502) simultaneously retrieves a rock core (516). The rock core (516) may be held in place by the core catcher (504) and stored in the inner barrel (506). Once the rock core (516) reaches the end (518) of the inner barrel (506), an overshot (not shown) may be deployed downhole to retrieve the inner barrel (506) that contains the rock core (516). Once the inner barrel (506) is on the surface (110), the rock core (516) is removed from the inner barrel (506).

The extracted rock core (516) may be up to 15 centimeters in diameter and approximately ten meters long. To prepare the rock core (516) for testing in a laboratory setting, the rock core (516) may be cut and ground into core plugs. A core plug may be a few centimeters in diameter and approximately five centimeters long, though other shapes and dimensions may be used. Further, a core plug may be cut and ground along a particular axis, such as parallel or perpendicular to an axis of the well (514) being drilled. Hereinafter, a core plug will be referred to as simply a "rock sample."

The rock sample may be dried to remove fluids, such as water and hydrocarbons. In some embodiments, the rock sample may be placed in a vacuum oven to remove the fluids. The rock sample may also be pre-stressed to remove inelastic deformation.

Figure 6B:
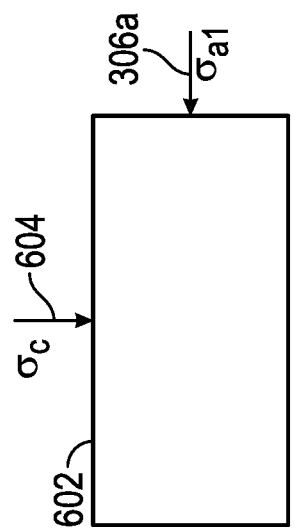
FIG. 6B shows a rock sample in accordance with one or more embodiments.
Figure 6A:
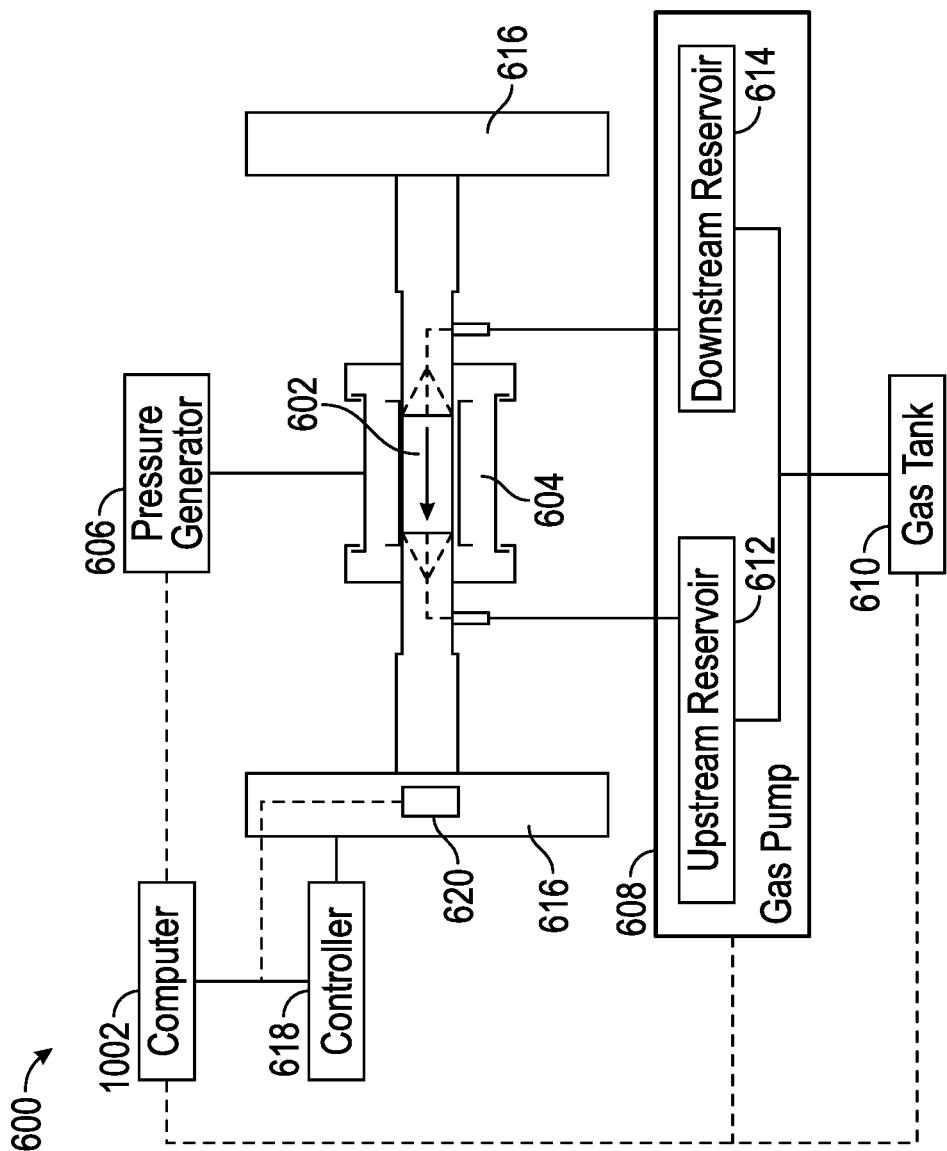
FIG. 6A illustrates a permeability system in accordance with one or more embodiments.

The rock sample may be pre-stressed as well as subjected to the previously defined first sequence of CSASPP triplets (400) and second sequence of CSASPP triplets (410) using a permeability system. FIG. 6A illustrates a permeability system (600) in accordance with one or more embodiments. Hereinafter, the application of the first sequence of CSASPP triplets (400) and/or the second sequence of CSASPP triplets (410) to the rock sample (602) may be simply referred to as a "test" or "testing." During pre-stressing or testing, the rock sample (602) is housed in a core holder or jacket (604). In some embodiments, the jacket (604) may be a hollow Viton sleeve. A pressure generator (606) connected to the jacket (604) may be configured to control the confining stress $\sigma_c$ (304) applied to the rock sample (602).

In some embodiments, the pressure generator (606) may also be configured to control one or more axial stresses $\sigma_a$ (306a). In these embodiments, $\sigma_c = \sigma_a$. In other embodiments, one or more actuators (616) may be configured to control one or more axial stresses $\sigma_a$ (306a). In these embodiments, the axial stress $\sigma_a$ (306a) controlled by the actuator (616) may be different than the confining stress $\sigma_c$ (304). For reference, the permeability system (600) shown in FIG. 6A is configured such that the pressure generator (606) applies the confining stress $\sigma_c$ (304) and axial stress $\sigma_a$ (306a) to the rock sample (602) where $\sigma_c = \sigma_a$. Returning to FIG. 6A, the actuators (616) may be controlled by servomotors (not shown) within or neighboring a controller (618). Further, the actuators (616) may be placed in series with a load cell (620) that measures axial stress $\sigma_a$ (306a).

The permeability system (600) may also include a gas pump (608) that connects to each end of the rock sample (602) configured to control pore pressure $p_p$ (302). To control pore pressure $p_p$ (302), a gas tank (610) may supply helium, nitrogen, or other gas into the pores (206) of the rock sample (602) via an upstream reservoir (612) and/or a downstream reservoir (614) within the gas pump (608). Note that in some embodiments, the upstream reservoir (612) and the downstream reservoir (614) may each be controlled by separate gas pumps (608) and/or separate gas tanks (610). The upstream reservoir (612) and downstream reservoir (614) may also be used to recover gas from the rock sample (602) depending on the mode of operation of the gas pump (608). For example, if a hydrostatic pore pressure $p_p$ (302) is applied to the rock sample (602), both the upstream reservoir (612) and downstream reservoir (614) may supply gas to the rock sample (602). However, if a pressure pulse is applied to the rock sample (602), the upstream reservoir (612) may supply gas to the rock sample (602) while the downstream reservoir (614) recovers the gas that passed though the rock sample (602).

In some embodiments, the permeability system (600) may be contained within a temperature-controlled housing (not shown). In some embodiments, various parts of the permeability system (600) may be communicably coupled to a computer (1002). A computer (1002) will be described in reference to FIG. 10. The computer (1002) may supply instructions to and/or collect data from the pressure generator (606), the gas tank (610), the gas pump (608), the controller (618), and/or the load cell (620).

During testing, each CSASPP triplet (404) among either sequence of CSASPP triplets (400, 410) is applied to the rock sample (602) statically in series. While the rock sample (602) is subjected to each CSASPP triplet (404), permeability k is determined. Permeability k may be determined using indirect methods, such as a pressure pulse decay method or steady-state Darcy flow method. The pressure pulse decay method may take on the order of hours. The steady-state Darcy flow method may take on the order of hours or even days. In brief, the pressure pulse decay method may rely on the gas pump (608) to emit small pressure pulses at the upstream reservoir (612) that diffuse through the rock sample (602) to the downstream reservoir (614). In some embodiments, each pressure pulse may be small to minimize changes in pore pressure $p_p$ (302). For each pressure pulse, a sample pressure differential is determined in the rock sample (602) as a function of time. The sample pressure differential for each CSASPP triplet (404) may then be fit to a permeability-pressure model to determine permeability k. Determining permeability k for each of the first sequence of CSASPP triplets (400) may generate a first sequence of permeabilities. Similarly, determining permeability k for each of the second sequence of CSASPP triplets (410) may generate a second sequence of permeabilities.

Figure 7A:
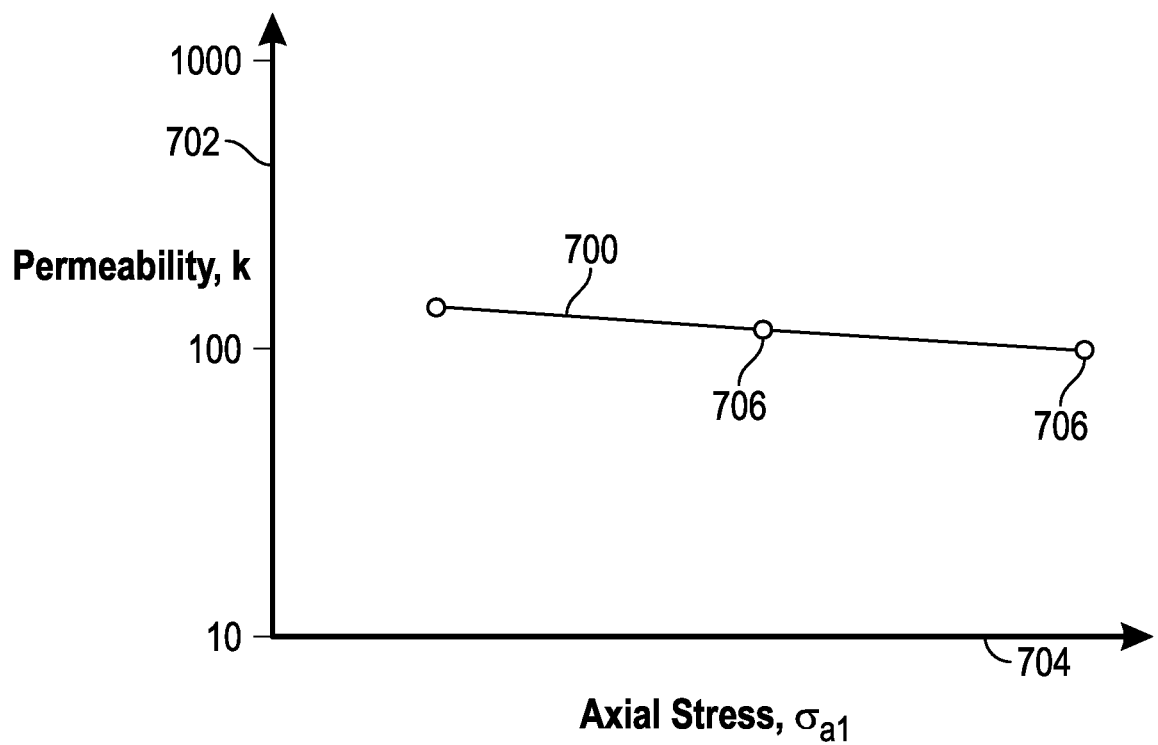
FIGS. 7A and 7B show relationships in accordance with one or more embodiments.

The first sequence of CSASPP triplets (400), at least in part, and the first sequence of permeabilities may be used to determine a first relationship (700) as shown in FIG. 7A. Note that FIG. 7A shows a semi-logarithmic scale. Permeability k presents on the ordinate (702) using a logarithmic scale and axial stress $\sigma_a$ (306a) presents on the abscissa (704) using a linear scale. Each point (706) shown by a circle represents a permeability k from the first sequence of permeabilities and an axial stress $\sigma_a$ (306a) from the first sequence of CSASPP triplets (400) both of which correspond to the same triplet number $s_1$. In some embodiments, the axial stress $\sigma_a$ (306a) associated to each point (706) is the actual axial stress $\sigma_a$ (306a) applied to the rock sample (602) during testing rather than the defined axial stress $\sigma_a$ (306a) as the two values may be slightly different.

The first relationship (700) fit to the points (706) may take the linear form of:

$$y_1 = a_1 x_1 + b_1, \qquad \text{Equation (6)}$$

where $y_1$ is the natural logarithm of the first sequence of permeabilities, $x_1$ is the axial stresses $\sigma_a$ (306a) among the first sequence of CSASPP triplets (400), and $a_1$ and $b_1$ are estimated constants. However, a person of ordinary skill in the art will appreciate that the first relationship (700) may take forms other than the one presented in Equation (6), such as an exponential form.

A first rock parameter may be extracted from the first relationship (700) assuming a first permeability model. Recall that in some embodiments, the first permeability model may be Equation (5) with the first stress model of Equation (3) embedded into Equation (5). Note that the first stress model of Equation (3) includes the first stress sensitivity parameter $\gamma$. Assuming the first permeability model is Equation (3) embedded into Equation (5), the following relation may be formed:

$$a_1 \approx \beta\gamma, \qquad \text{Equation (7)}$$

where $a_1$ is the slope of the first relationship (700) as well as the first rock parameter.

Figure 7B:
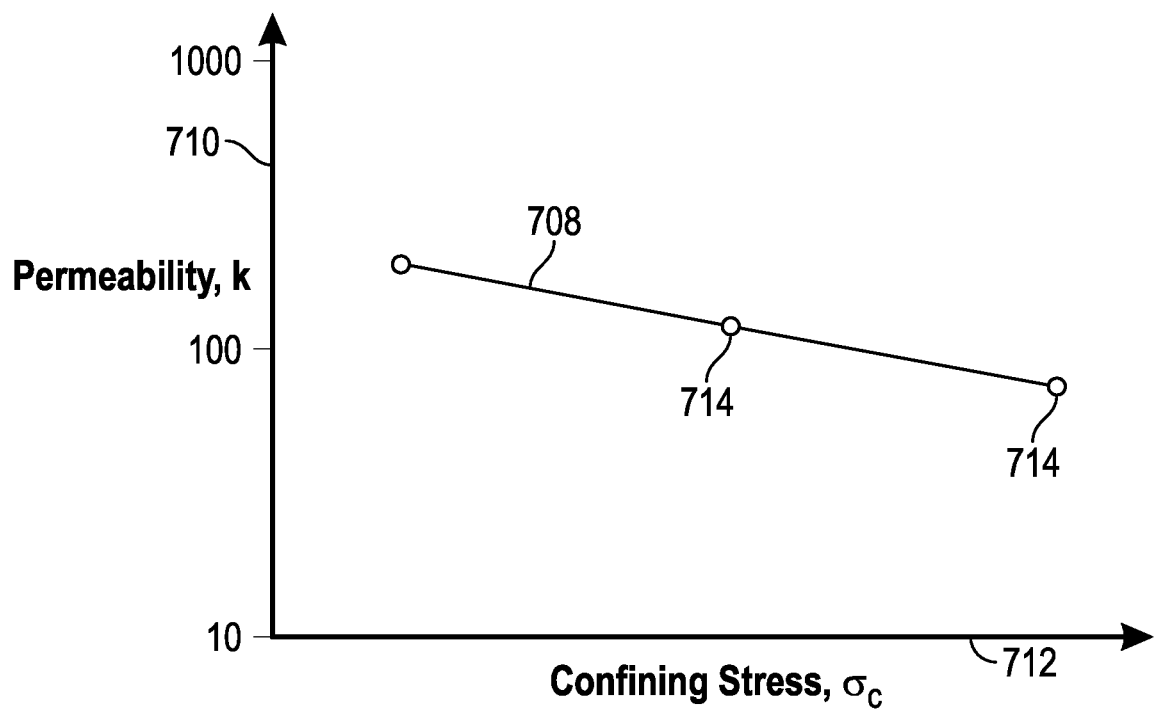

Turning to FIG. 7B, the second sequence of CSASPP triplets (410), at least in part, and the second sequence of permeabilities may be used to determine a second relationship (708). Like FIG. 7A, FIG. 7B shows a semi-logarithmic scale. Permeability k presents on the ordinate (710) using a logarithmic scale and confining stress $\sigma_c$ (304) presents on the abscissa (712) using a linear scale. Each point (714) shown by a circle represents a permeability k from the second sequence of permeabilities and a confining stress $\sigma_c$ (304) from the second sequence of CSASPP triplets (410) both of which correspond to the same triplet number $s_2$. In some embodiments, the confining stress $\sigma_c$ (304) associated to each point (714) is the actual confining stress $\sigma_c$ (304) applied to the rock sample (602) during testing rather than the defined confining stress $\sigma_c$ (304) as the two values may be slightly different.

The second relationship (708) fit to the points (714) may then take the linear form of:

$$y_2 = a_2 x_2 + b_2, \qquad \text{Equation (8)}$$

where $y_2$ is the natural logarithm of the second sequence of permeabilities, $x_2$ is the confining stresses $\sigma_c$ (304) among the second sequence of CSASPP triplets (410), and $a_2$ and $b_2$ are estimated constants.

A second rock parameter may be extracted from the second relationship (708) assuming the same first permeability model that was assumed in reference to FIG. 7A. The following relation may then be formed:

$$a_2 \approx \beta(1 - \gamma),\quad \text{Equation (9)}$$

where $a_2$ is the slope of the second relationship (708) as well as the second rock parameter.

A first stress sensitivity parameter $\gamma$ may then be determined using the first rock parameter $a_1$ and the second rock parameter $a_2$. In some embodiments, the first stress sensitivity parameter $\gamma$ may be determined using the ratio:

$$\gamma \approx \frac{a_1}{a_1 + a_2}.\quad \text{Equation (10)}$$

However, a person of ordinary skill in the art will appreciate that different first stress sensitivity parameters $\gamma$ may be determined from relationships other than Equation (10).

Figure 8:
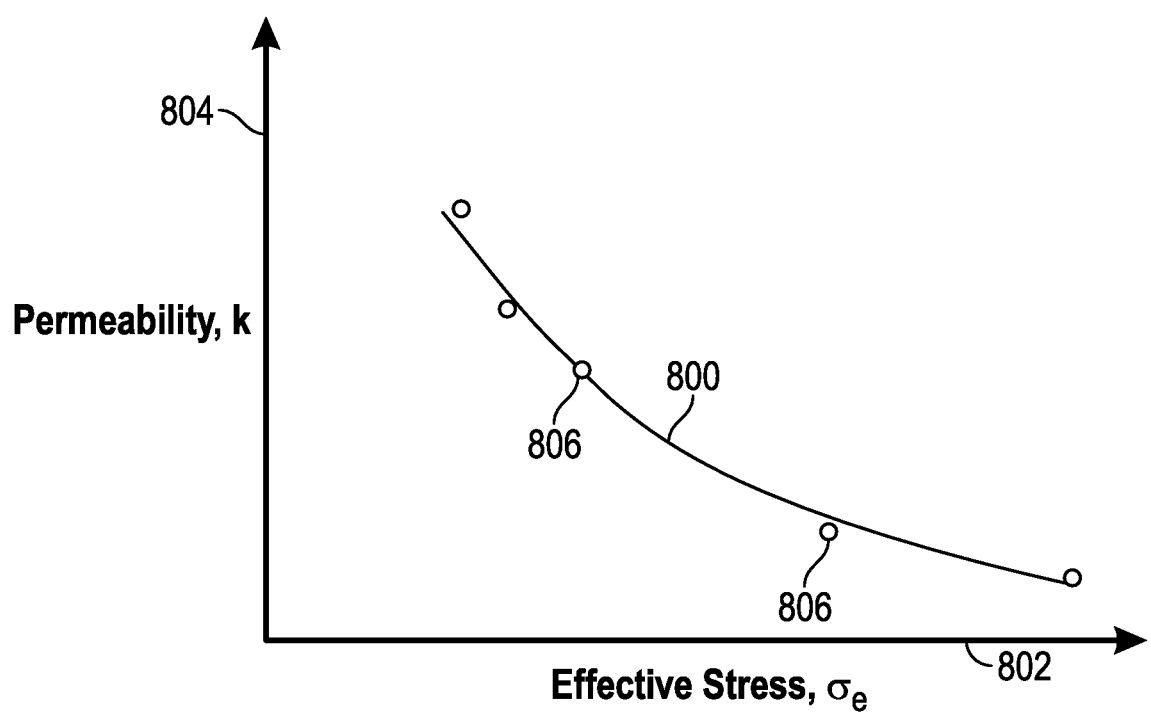
FIG. 8 shows a relationship in accordance with one or more embodiments.

Turning to FIG. 8, a third relationship (800) may be determined using the first sequence of CSASPP triplets (400), the first sequence of permeabilities, the second sequence of CSASPP triplets (410), the second sequence of permeabilities, the first stress sensitivity parameter $\gamma$, and the first permeability model used in reference to FIGS. 7A and 7B. In some embodiments, the effective stress $\sigma_e$ may be determined using the first stress model presented in Equation (3) assuming deviatoric stress $\sigma_d$ is defined by Equation (1) for each CSASPP triplet (404) among both sequences of CSASPP triplets (400, 410). In these embodiments, the Biot coefficient $\beta$ may be assumed or previously determined. Further to these embodiments, the first stress sensitivity parameter $\gamma$ determined previously may be used. FIG. 8 presents the determined effective stresses $\sigma_e$ on the abscissa (802) and both sequences of permeabilities on the ordinate (804). Each point (806) shown by a circle represents a permeability k from either sequence of permeabilities and an effective stress $\sigma_e$ determined from either sequence of CSASPP triplets (400, 410) both of which correspond to the same triplet number $s_1$ or $s_2$.

The third relationship (800) fit to the points (806) may then take the form of:

$$y_3 = ce^{dx_3},\quad \text{Equation (11)}$$

where $y_3$ is both sequences of permeabilities, $x_3$ is effective stress $\sigma_e$ determined from both sequences of CSASPP triplets (400, 410), at least in part, and c and d are estimated constants.

Assuming the same first permeability model previously used relative to FIGS. 7A and 7B:

$$c \approx k_0, \text{ and}\quad \text{Equation (12)}$$

$$d \approx -\alpha.\quad \text{Equation (13)}$$

Recall that $k_0$ is initial permeability and $\alpha$ is a second stress sensitivity parameter.

Figure 9:
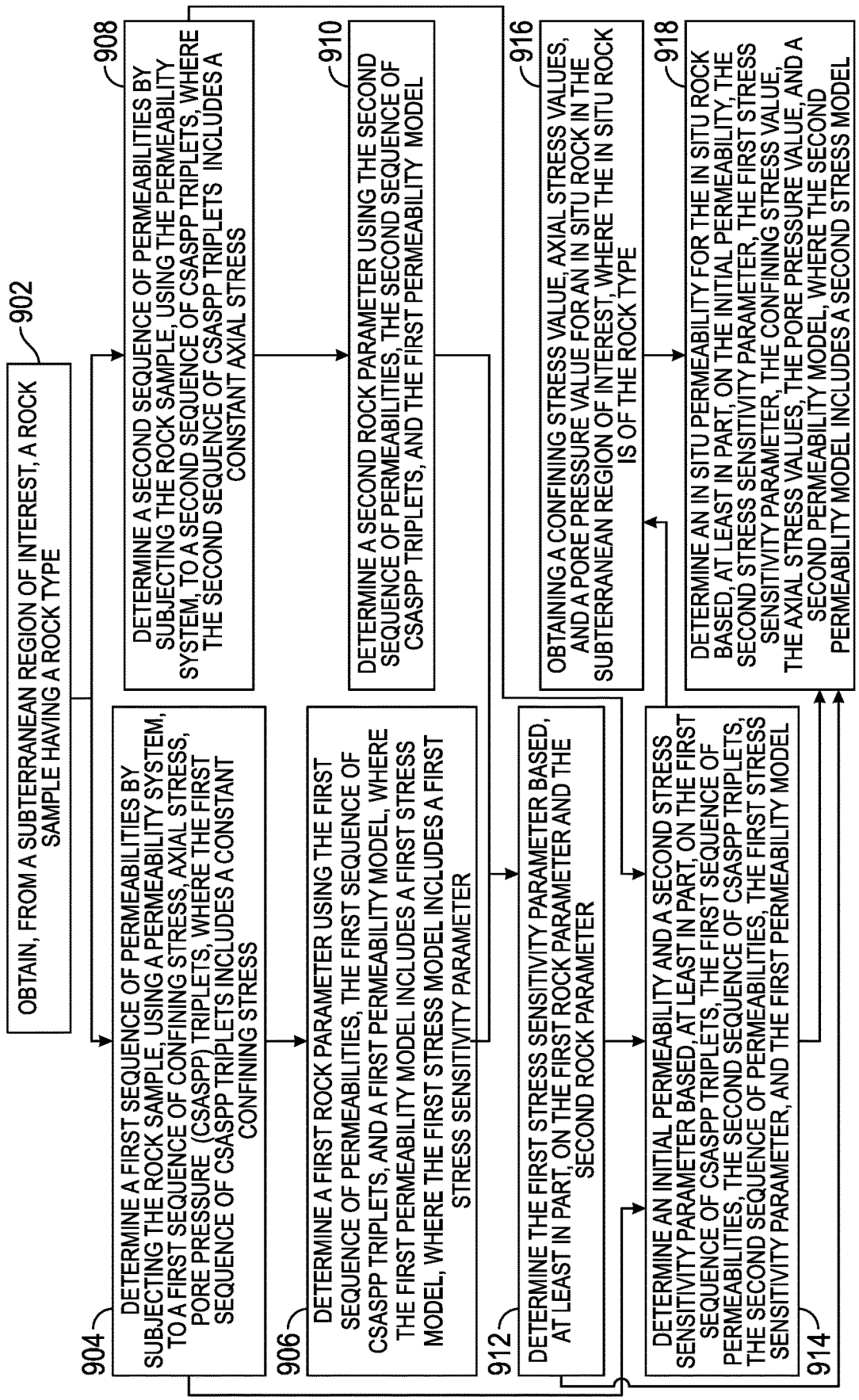
FIG. 9 shows a flowchart in accordance with one or more embodiments.

FIG. 9 describes a method in accordance with one or more embodiments. In step 902, a rock sample (602) is obtained from a subterranean region of interest (100). The rock sample (602) may be obtained from the subterranean region of interest (100) using a rock sample extraction tool. In some embodiments, the rock sample extraction tool may be a coring system (500) as described in FIG. 5. The rock sample (602) has a rock type, such as but not limited to sandstone, carbonate, or shale. The rock sample (602) may also be rock where the pores (206) are saturated with natural gas or other hydrocarbons.

In step 904, a first sequence of permeabilities is determined. The first sequence of permeabilities may be determined by subjecting the rock sample (602) to each of a first sequence of CSASPP triplets (400) statically in series. Each of the first sequence of permeabilities is determined for each of the first sequence of CSASPP triplets (400). The first sequence of CSASPP triplets (400) may be defined such that the values of confining stress $\sigma_c$ (304) among the first sequence of CSASPP triplets (400) are constant as shown in FIG. 4A.

To determine each of the first sequence of permeabilities, the rock sample (602) may be subjected to each of the first sequence of CSASPP triplets (400) using a permeability system (600) as described in FIG. 6A. With the rock sample (602) in the permeability system (600), the first CSASPP triplet (404) among the first sequence of CSASPP triplets (400) is applied to the rock sample (602) statically. In some embodiments, a method to determine permeability k is concurrently applied to the rock sample (602) for each CSASPP triplet (404). The method to determine permeability k may be, but is not limited to, a pressure pulse decay method or a steady-state Darcy flow method. Once the method to determine the permeability k is complete, the second CSASPP triplet (404) among the first sequence of CSASPP triplets (400) is applied to the rock sample (602) statically and a method to determine permeability k applied to the rock sample (602). This process is repeated until a permeability k has been determined for each of the first sequence of CSASPP triplets (400). In some embodiments, the same method to determine permeability k for each CSASPP triplet (404) is used. In other embodiments, different methods may be used to determine permeability k within the first sequence of permeabilities.

In step 906, a first rock parameter $a_1$ is determined. The first rock parameter $a_1$ is determined using the first sequence of permeabilities, the first sequence of CSASPP triplets (400), and a first permeability model. In some embodiments, a first relationship (700) may be determined using the first sequence of permeabilities and the first sequence of CSASPP triplets (400) as described in FIG. 7A. In some embodiments, the first permeability model may be Equation (3) embedded into Equation (5). In these embodiments, the first rock parameter $a_1$ may then be determined using Equation (7) as described in reference to FIG. 7A.

In step 908, a second sequence of permeabilities is determined. The second sequence of permeabilities may be determined by subjecting the rock sample (602) to each of a second sequence of CSASPP triplets (410) statically in series. Each of the second sequence of permeabilities is determined for each of the second sequence of CSASPP triplets (410). The second sequence of CSASPP triplets (410) is defined such that the values of axial stress $\sigma_a$ (306a) among the second sequence of CSASPP triplets (410) are constant as shown in FIG. 4B.

Each of the second sequence of permeabilities may be determined following a similar process as is described in step 904 only now each of the second sequence of CSASPP triplets (410) is applied to the rock sample (602) using the permeability system (600).

In step 910, a second rock parameter $a_2$ is determined. The second rock parameter $a_2$ is determined using the second sequence of permeabilities, the second sequence of CSASPP triplets (410), and the first permeability model from step 906. In some embodiments, a second relationship (708) may be determined using the second sequence of permeabilities and the second sequence of CSASPP triplets (410) as described in FIG. 7B. The second rock parameter $a_2$ may then be determined using Equation (9) as described in reference to FIG. 7B.

In step 912, a first stress sensitivity parameter $\gamma$ is determined. In some embodiments, the first stress sensitivity parameter $\gamma$ may be determined using the first rock parameter $a_1$ determined in step 906 and the second rock parameter $a_2$ determined in step 910. In some embodiments, the first stress sensitivity parameter $\gamma$ may be determined using Equation (10).

In step 914, an initial permeability $k_0$ and a second stress sensitivity parameter $\alpha$ are determined. The initial permeability $k_0$ and the second stress sensitivity parameter $\alpha$ may be determined using the first sequence of CSASPP triplets (400) and the first sequence of permeabilities from step 904, the second sequence of CSASPP triplets (410) and the second sequence of permeabilities from step 908, the first stress sensitivity parameter $\gamma$ from step 912, and the first permeability model. As described relative to FIG. 8, effective stress $\sigma_e$ may be determined using the first stress model presented in Equation (3) assuming deviatoric stress $\sigma_d$ is defined by Equation (1) for each CSASPP triplet (404) among both sequences of CSASPP triplets (400, 410). In other embodiments, deviatoric stress $\sigma_d$ may be defined differently than Equation (1). In some embodiments, the Biot coefficient $\beta$ may be assumed or previously determined. A third relationship (800) may then be determined as described in FIG. 8. The initial permeability $k_0$ and the second stress sensitivity parameter $\alpha$ may then be extracted from the third relationship (800) using Equations (12) and (13).

In step 916, a confining stress value, axial stress values, and a pore pressure value for an in situ rock (102) in the subterranean region of interest (100) are obtained. In some embodiments, the confining stress value, axial stress values, and pore pressure value may be determined from well logs and/or surface seismic data. In this step, the in situ rock (102) in the subterranean of interest (100) is of the same rock type as the rock sample (602).

In step 918, in situ permeability k for the in situ rock (102) is determined. In situ permeability k is determined using a second permeability model. The second permeability model may be an extension of the first permeability model. In some embodiments, the second permeability model may be Equation (5) with Equation (4) embedded into it. In these embodiments, the second stress model presented in Equation (4) includes a confining stress $\sigma_c$ (304) and two axial stresses $\sigma_{a1}$ and $\sigma_{a2}$ (306a, b). A person of ordinary skill in the art will appreciate that the second permeability model may be equations other than Equation (4) embedded into Equation (5).

In these embodiments, the first stress sensitivity parameter $\gamma$ from step 912, the confining stress value, the axial stress values, and the pore pressure value from step 916, and an assumed or previously determined Biot coefficient $\beta$ may be input into Equation (4) to determine an in situ effective stress value. The in situ effective stress value as well as the initial permeability $k_0$ and the second stress sensitivity parameter $\alpha$ from step 914 may be input into Equation (5) to determine an in situ permeability value.

In situ permeability k of in situ rock (102) may be determined for in situ rock (102) at various depths, horizontal positions, and times within the subterranean region of interest (100). In situ permeability k may then be used, at least in part, to determine a hydrocarbon production rate. In some embodiments, a computer (1002) as will be described in FIG. 10 may be configured to determine the hydrocarbon production rate using the in situ permeability k.

The hydrocarbon production rate may be used, at least in part, to determine a production management plan. The production management plan may reside and/or be adjusted within production management software (1010) stored on a memory (1006) of a computer (1002) as will be described relative to FIG. 10. The production management plan may define and organize the activities associated with producing hydrocarbons from a hydrocarbon reservoir (106). For example, a production management plan may define how rapidly to produce hydrocarbons for various time intervals for each well (514) over the lifetime of each well (514). A production management plan may also define when and where to drill new wells (514) and how to complete the new wells (514) that penetrate the hydrocarbon reservoir (106). Further, a production management plan may define when, where, and how to stimulate existing and new wells (514). Further still, a production management plan may define when to abandon a well (514).

Figure 10:
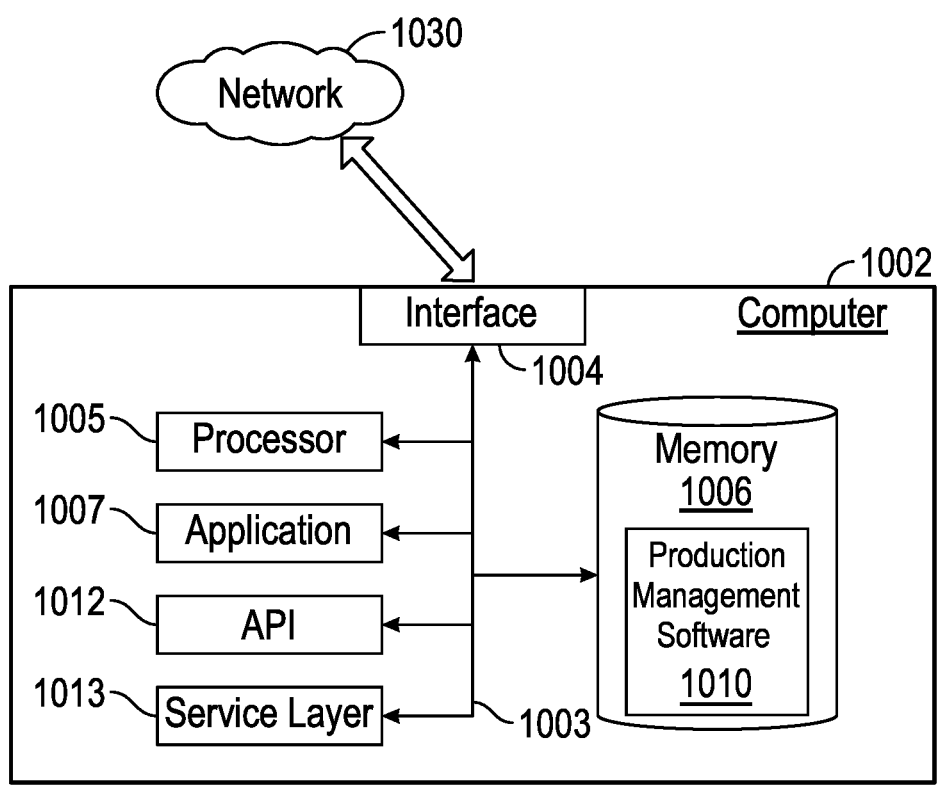
FIG. 10 illustrates a computer in accordance with one or more embodiments.

FIG. 10 depicts a block diagram of a computer system (1002) used to provide computational functionalities associated with described algorithms, methods, functions, processes, flows, and procedures as described in this disclosure, according to one or more embodiments. The illustrated computer (1002) is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer (1002) may include a computer that includes an input device, such as a keypad, keyboard, touch screen, or other device that can accept user information, and an output device that conveys information associated with the operation of the computer (1002), including digital data, visual, or audio information (or a combination of information), or a GUI.

The computer (1002) can serve in a role as a client, network component, a server, a database or other persistency, or any other component (or a combination of roles) of a computer system for performing the subject matter described in the instant disclosure. The illustrated computer (1002) is communicably coupled with a network (1030). In some implementations, one or more components of the computer (1002) may be configured to operate within environments, including cloud-computing-based, local, global, or other environment (or a combination of environments).

At a high level, the computer (1002) is an electronic computing device operable to receive, transmit, process, store, or manage data and information associated with the described subject matter. According to some implementations, the computer (1002) may also include or be communicably coupled with an application server, e-mail server, web server, caching server, streaming data server, business intelligence (BI) server, or other server (or a combination of servers).

The computer (1002) can receive requests over network (1030) from a client application (for example, executing on another computer (1002)) and responding to the received requests by processing the said requests in an appropriate software application. In addition, requests may also be sent to the computer (1002) from internal users (for example, from a command console or by other appropriate access method), external or third-parties, other automated applications, as well as any other appropriate entities, individuals, systems, or computers.

Each of the components of the computer (1002) can communicate using a system bus (1003). In some implementations, any or all of the components of the computer (1002), both hardware or software (or a combination of hardware and software), may interface with each other or the interface (1004) (or a combination of both) over the system bus (1003) using an application programming interface (API) (1012) or a service layer (1013) (or a combination of the API (1012) and service layer (1013). The API (1012) may include specifications for routines, data structures, and object classes. The API (1012) may be either computer-language independent or dependent and refer to a complete interface, a single function, or even a set of APIs. The service layer (1013) provides software services to the computer (1002) or other components (whether or not illustrated) that are communicably coupled to the computer (1002). The functionality of the computer (1002) may be accessible for all service consumers using this service layer. Software services, such as those provided by the service layer (1013), provide reusable, defined business functionalities through a defined interface. For example, the interface may be software written in JAVA, C++, or other suitable language providing data in extensible markup language (XML) format or another suitable format. While illustrated as an integrated component of the computer (1002), alternative implementations may illustrate the API (1012) or the service layer (1013) as stand-alone components in relation to other components of the computer (1002) or other components (whether or not illustrated) that are communicably coupled to the computer (1002). Moreover, any or all parts of the API (1012) or the service layer (1013) may be implemented as child or sub-modules of another software module, enterprise application, or hardware module without departing from the scope of this disclosure.

The computer (1002) includes an interface (1004). Although illustrated as a single interface (1004) in FIG. 10, two or more interfaces (1004) may be used according to particular needs, desires, or particular implementations of the computer (1002). The interface (1004) is used by the computer (1002) for communicating with other systems in a distributed environment that are connected to the network (1030). Generally, the interface (1004) includes logic encoded in software or hardware (or a combination of software and hardware) and operable to communicate with the network (1030). More specifically, the interface (1004) may include software supporting one or more communication protocols, such as the Wellsite Information Transfer Specification (WITS) protocol, associated with communications such that the network (1030) or interface's hardware is operable to communicate physical signals within and outside of the illustrated computer (1002).

The computer (1002) includes at least one computer processor (1005). Although illustrated as a single computer processor (1005) in FIG. 10, two or more processors may be used according to particular needs, desires, or particular implementations of the computer (1002). Generally, the computer processor (1005) executes instructions and manipulates data to perform the operations of the computer (1002) and any algorithms, methods, functions, processes, flows, and procedures as described in the instant disclosure.

The computer (1002) also includes a memory (1006) that holds data for the computer (1002) or other components (or a combination of both) that can be connected to the network (1030). For example, memory (1006) may store production management software (1010). Although illustrated as a single memory (1006) in FIG. 10, two or more memories may be used according to particular needs, desires, or particular implementations of the computer (1002) and the described functionality. While memory (1006) is illustrated as an integral component of the computer (1002), in alternative implementations, memory (1006) can be external to the computer (1002).

The application (1007) is an algorithmic software engine providing functionality according to particular needs, desires, or particular implementations of the computer (1002), particularly with respect to functionality described in this disclosure. For example, application (1007) can serve as one or more components, modules, applications, etc. Further, although illustrated as a single application (1007), the application (1007) may be implemented as multiple applications (1007) on the computer (1002). In addition, although illustrated as integral to the computer (1002), in alternative implementations, the application (1007) can be external to the computer (1002).

There may be any number of computers (1002) associated with, or external to, a computer system containing a computer (1002), where each computer (1002) communicates over network (1030). Further, the term "client," "user," and other appropriate terminology may be used interchangeably as appropriate without departing from the scope of this disclosure. Moreover, this disclosure contemplates that many users may use one computer (1002), or that one user may use multiple computers (1002).

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. A method comprising:
   obtaining, from a subterranean region of interest, a rock sample having a rock type;
   determining a first sequence of permeabilities by subjecting the rock sample, using a permeability system, to a first sequence of confining stress, axial stress, pore pressure (CSASPP) triplets, wherein the first sequence of CSASPP triplets comprises a constant confining stress;
   determining a first rock parameter using the first sequence of permeabilities, the first sequence of CSASPP triplets, and a first permeability model, wherein the first permeability model comprises a first stress model, wherein the first stress model comprises a first stress sensitivity parameter;
   determining a second sequence of permeabilities by subjecting the rock sample, using the permeability system, to a second sequence of CSASPP triplets, wherein the second sequence of CSASPP triplets comprises a constant axial stress;
   determining a second rock parameter using the second sequence of permeabilities, the second sequence of CSASPP triplets, and the first permeability model;

determining the first stress sensitivity parameter based, at least in part, on the first rock parameter and the second rock parameter;

determining, using a computer processor, an initial permeability and a second stress sensitivity parameter based, at least in part, on the first sequence of CSASPP triplets, the first sequence of permeabilities, the second sequence of CSASPP triplets, the second sequence of permeabilities, the first stress sensitivity parameter, and the first permeability model;

obtaining an in situ confining stress value, in situ axial stress values, and an in situ pore pressure value for an in situ rock in the subterranean region of interest, wherein the in situ rock is of the rock type; and determining an in situ permeability for the in situ rock based, at least in part, on the initial permeability, the second stress sensitivity parameter, the first stress sensitivity parameter, the in situ confining stress value, the in situ axial stress values, the in situ pore pressure value, and a second permeability model, wherein the second permeability model comprises a second stress model.

2. The method of claim 1, wherein the rock sample comprises source rock.

3. The method of claim 1, wherein the rock type comprises shale.

4. The method of claim 1, further comprising:
determining a hydrocarbon production rate based, at least in part, on the in situ permeability; and
determining a production management plan based, at least in part, on the hydrocarbon production rate.

5. The method of claim 4, further comprising stimulating a well within the subterranean region of interest based, at least in part, on the production management plan.

6. The method of claim 1, wherein obtaining the rock sample further comprises:
cutting the rock sample;
drying the rock sample; and
pre-stressing the rock sample.

7. The method of claim 1, wherein a pore pressure among the first sequence of CSASPP triplets is selected to minimize Knudsen diffusion.

8. The method of claim 7, wherein the pore pressure is greater than 17 megapascals.

9. The method of claim 1, wherein the first rock parameter comprises the first stress sensitivity parameter.

10. The method of claim 1, wherein determining the first sequence of permeabilities comprises a pressure pulse decay method.

11. The method of claim 10, wherein the pressure pulse decay method comprises:
obtaining a permeability-pressure model;
subjecting a test sample to a CSASPP triplet;
generating a pressure pulse;
determining a test sample pressure differential in the test sample as a function of time due to the pressure pulse; and
determining a permeability by fitting, in part, the test sample pressure differential as the function of time to the permeability-pressure model.

12. The method of claim 1, wherein the first stress sensitivity parameter comprises a ratio of the first rock parameter and a summation of the first rock parameter and the second rock parameter.

13. A system comprising:
a permeability system configured to subject a rock sample, from a subterranean region of interest, having a rock type to a first sequence of confining stress, axial stress, pore pressure (CSASPP) triplets and a second sequence of CSASPP triplets; and a computer system configured to:
determine a first sequence of permeabilities following the rock sample being subjected to the first sequence of CSASPP triplets using the permeability system, wherein the first sequence of CSASPP triplets comprises a constant confining stress, determine a first rock parameter using the first sequence of permeabilities, the first sequence of CSASPP triplets, and a first permeability model, wherein the first permeability model comprises a first stress model, wherein the first stress model comprises a first stress sensitivity parameter, determine a second sequence of permeabilities following the rock sample being subjected to the second sequence of CSASPP triplets using the permeability system, wherein the second sequence of CSASPP triplets comprises a constant axial stress, determine a second rock parameter using the second sequence of permeabilities, the second sequence of CSASPP triplets, and the first permeability model, determine the first stress sensitivity parameter based, at least in part, on the first rock parameter and the second rock parameter, determine an initial permeability and a second stress sensitivity parameter based, at least in part, on the first sequence of CSASPP triplets, the first sequence of permeabilities, the second sequence of CSASPP triplets, the second sequence of permeabilities, the first stress sensitivity parameter, and the first permeability model, receive an in situ confining stress value, in situ axial stress values, and an in situ pore pressure value for an in situ rock in the subterranean region of interest, wherein the in situ rock is of the rock type, and determine an in situ permeability for the in situ rock based, at least in part, on the initial permeability, the second stress sensitivity parameter, the first stress sensitivity parameter, the in situ confining stress value, the in situ axial stress values, the in situ pore pressure value, and a second permeability model, wherein the second permeability model comprises a second stress model.

14. The system of claim 13, wherein the computer system is further configured to determine a hydrocarbon production rate based, at least in part, on the in situ permeability.

15. The system of claim 14, further comprising production management software configured to determine a production management plan based, at least in part, on the hydrocarbon production rate.

16. The system of claim 13, further comprising a rock sample extraction tool configured to obtain the rock sample from the subterranean region of interest.

17. The system of claim 16, wherein the rock sample extraction tool comprises a coring system.

18. The system of claim 13, wherein the permeability system comprises:
a jacket for housing the rock sample;
a pressure generator configured to apply the confining stress to the rock sample;
an actuator configured to apply the axial stress to the rock sample; and a gas pump configured to apply the pore pressure to the
   rock sample, wherein the gas pump comprises:
   an upstream reservoir, and
   a downstream reservoir.

19. The system of claim 18, wherein the gas pump houses helium.

20. The system of claim 18, wherein the gas pump is configured to emit a pressure pulse.

* * * * *